US006410283B1

(12) United States Patent
Rehmat et al.

(10) Patent No.: US 6,410,283 B1
(45) Date of Patent: Jun. 25, 2002

(54) CONVERSION OF SEWAGE SLUDGE INTO ELECTRIC POWER

(75) Inventors: Amirali G. Rehmat, Darien; Anthony L. Lee, Glen Ellyn; Michael C. Mensinger, Darien; Anil Goyal, Willowbrook; S. Peter Barone, Bartlett, all of IL (US)

(73) Assignee: Endesco Clean Harbors, L.L.C., Des Plaines, IL (US)

( * ) Notice: Subject to any disclaimer, the term of this patent is extended or adjusted under 35 U.S.C. 154(b) by 0 days.

(21) Appl. No.: 09/876,325

(22) Filed: Jun. 7, 2001

(51) Int. Cl.[7] .............................. C12P 5/02; C02F 3/00; C02F 3/30
(52) U.S. Cl. .................... 435/167; 48/197 A; 210/603; 210/605; 210/609
(58) Field of Search .................. 435/167; 210/603, 210/609, 605; 48/197 A

(56) References Cited

U.S. PATENT DOCUMENTS 4,022,665 A 5/1977 Ghosh et al.
4,289,625 A * 9/1981 Tarman et al. ................ 21/603
4,316,961 A 2/1982 Klass et al.

FOREIGN PATENT DOCUMENTS

FR 2787103 * 6/2000

* cited by examiner

Primary Examiner—Herbert J. Lilling
(74) Attorney, Agent, or Firm—Mark E. Fejer

(57) ABSTRACT

A method for generating electricity in which sludge is anaerobically digested to form a gas mixture of methane and carbon dioxide and a residue of digested sludge. Water is removed from the digested sludge to form dewatered sludge, which, in turn, is gasified to form a gaseous composition which includes carbon monoxide and hydrogen. The gas mixture containing methane and carbon dioxide produced in the anaerobic digestion step is mixed with the gas mixture containing hydrogen and carbon monoxide from the gasification step and burned in an apparatus, such as a microturbine, for generating electricity. The non-carbonaceous fraction of the sludge is melted during the gasification step and rendered environmentally benign.

17 Claims, 1 Drawing Sheet

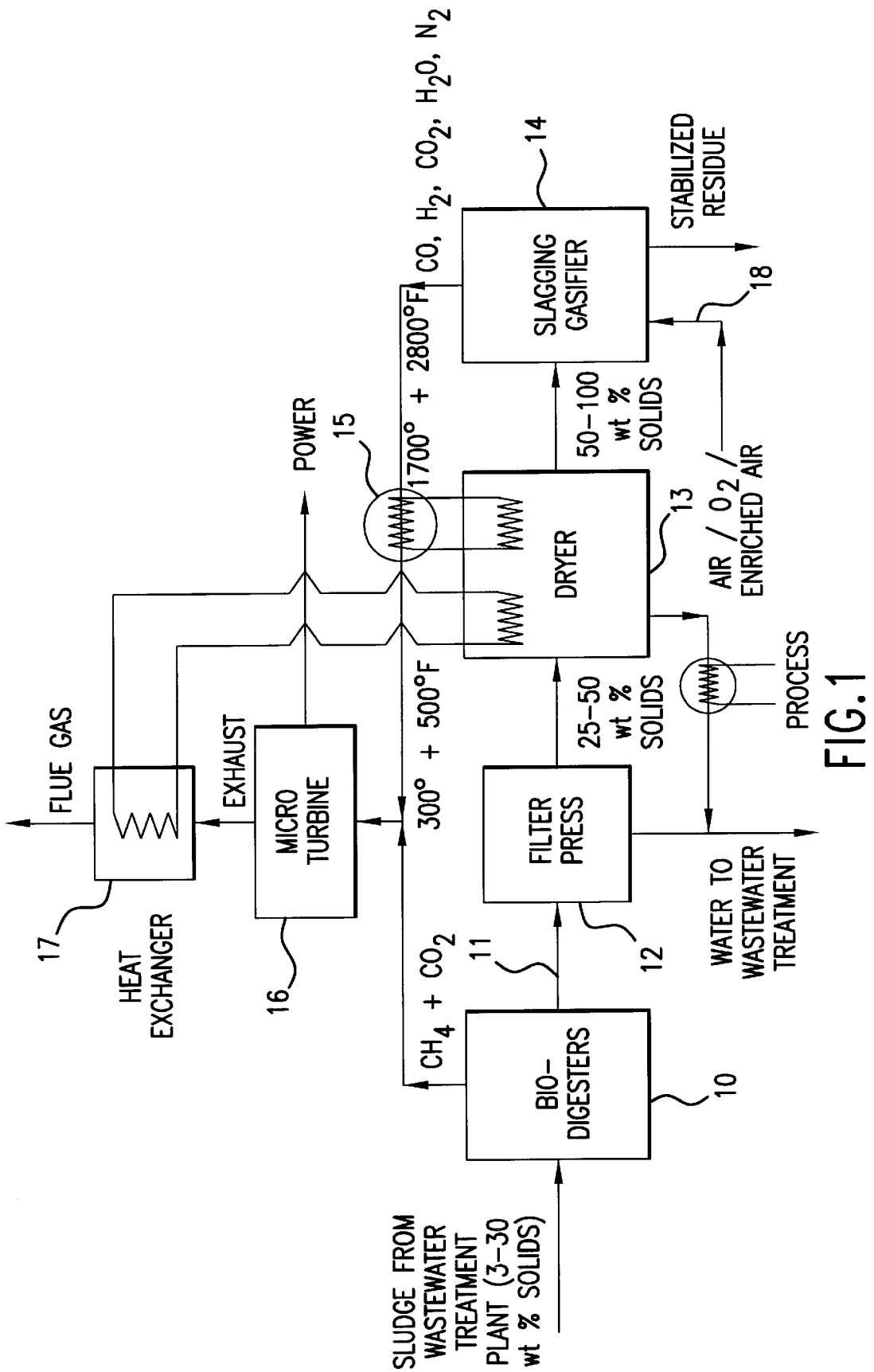

CONVERSION OF SEWAGE SLUDGE INTO ELECTRIC POWER

BACKGROUND OF THE INVENTION

1. Field of the Invention

This invention relates to a method for producing electricity utilizing a renewable resource, in particular, sewage sludge, in an efficient and environmentally responsible manner. More particularly, this invention relates to a multi-stage method for generating electricity from sewage sludge in which the sewage sludge is first anaerobically digested and the digested solids are then gasified.

2. Description of Related Art

To date, the utilization of sludge for the production of electricity has been hindered or has not been economical for a variety of reasons. First, the direct combustion of sewage sludge, in addition to being environmentally restrictive, is very inefficient due to its elevated water content, which exceeds 75 to 90% by weight. Second, because of its elevated water content, it is not economical to dry the sludge before it is used as a fuel for direct combustion. Third, the production of biogas from sewage sludge through the use of anaerobic bio-digesters has not been optimized. That is, digested solids that must eventually be discarded comprise a majority of the original sludge volume. And, finally, the disposal of sewage sludge, or biosolids, in landfills or its utilization for other applications, such as fertilizer or soil amendment, clearly needs to be examined in light of environmental issues relating to pathogens as well as organic and inorganic contaminants. The presence of inorganic and organic contaminants in digested sludge applied to the land clearly poses a potential danger to underground water supplies and eventually to human health.

It is apparent that there is a clear need for a process that not only achieves improvements in sludge utilization efficiency, but also does so in an environmentally safe manner.

SUMMARY OF THE INVENTION

Accordingly, it is one object of this invention to provide a method for converting sewage sludge to electricity having improved efficiency over conventional methods for utilizing sludge to produce electricity.

It is another object of this invention to provide a method for converting sewage sludge to electricity which addresses issues of efficiency arising from the substantial amount of water present in the sewage sludge.

It is yet another object of this invention to provide a method for converting sewage sludge to electricity which renders non-carbonaceous or inorganic components of the sludge environmentally benign.

These and other objects of this invention are addressed by a method for generating electricity in which the sewage sludge is first digested in an anaerobic digester forming a gas mixture of methane and carbon dioxide. Single-stage or multi-stage-anaerobic bio-digesters may be employed for this purpose. Water present in the digested sludge is then removed, forming dewatered sludge. The water may be removed by any of a number of known methods, such as filtration, centrifugation, and thermal drying. The dewatered sludge is then gasified in a cyclonic gasifier or other type of gasifier known to those skilled in the art to form a gas mixture comprising carbon monoxide and hydrogen. The gas mixture of methane and carbon dioxide from the anaerobic digester is mixed with the gas mixture comprising carbon monoxide and hydrogen from the gasifier and the resulting mixture is then burned in an apparatus suitable for generating electricity, such as a gas-fired turbine, resulting in the generation of electricity.

BRIEF DESCRIPTION OF THE DRAWINGS

These and other objects and features of this invention will be better understood from the following detailed description taken in conjunction with the drawings wherein:

FIG. 1 is a schematic diagram showing the method of this invention.

DETAILED DESCRIPTION OF PRESENTLY PREFERRED EMBODIMENTS

The invention disclosed herein is a multi-step method for achieving improved utility from sewage sludge as well as stabilizing any inorganic residue associated with the sludge. In the first step of the invention, after completion of the conventional sedimentation/aerobic treatment/thickening process steps which are typically performed at a wastewater treatment facility, that sludge, which may contain in excess of 95 percent by weight water, is subjected to anaerobic digestion to produce a gas mixture containing methane and carbon dioxide in this step, in the range of about 40 percent to about 70 percent by weight of the carbonaceous solids present in the sludge are converted to gas, leaving behind a residue of digested sludge. As previously stated, one stage or two stage bio-digesters can be employed for this purpose. two-stage anaerobic digestion is taught, for example, by U.S. Pat. No. 4,022,665to Ghosh et al. and U.S. Pat. No. 4,316,961, to Klass et/al., which are incorporated herein in their entirety by reference.

In the next step of the method of this invention, the residue of digested sludge is separated from water present therein by any suitable means known to those skilled in the art, including the use of a centrifuge, filter press, or filter, or the use of a dryer, or the use of a combination of these methods. After removal of the water from the digested sludge, the solids content in the remainder of the sludge may increase to as much as about 80 to 90 percent by weight of the sludge. This "dewatered" sludge is then subjected to a molten gasification step in which the dewatered sludge is reacted with oxygen, air or oxygen-enriched air at substoichiometric conditions. The primary objective of this step is to convert the carbonaceous material remaining in the sludge after the anaerobic digestion step into a gaseous fuel comprising primarily carbon monoxide and hydrogen. A further objective of this step is to convert the non-carbonaceous or inorganic component of the sludge, if any, into an environmentally benign residue.

FIG. 1 is a schematic diagram showing the process for converting sewage sludge to electric power in accordance with the method of this invention. As shown, sludge from a wastewater treatment facility comprising in the range of about 3% to about 30% by weight solids is introduced into bio-digesters 10 resulting in the formation of methane and carbon dioxide. The water content of the sludge emerging from bio-digesters 10 through line 11 is reduced by using dewatering processes such as filtration by means of filter press 12, centrifugation (not shown) and/or drying in dryer 13. Water removed during the dewatering process may then be returned to the wastewater treatment facility. As shown, the energy required for drying the sludge in dryer 13 may be provided by the cooling of gas exiting from gasifier 14 in heat exchanger 15, waste gas available from micro-turbine 16 in heat exchanger 17 and/or from the combustion of bio-digester gas. Using these dewatering processes results in an increase in solids content in the sludge into the range of about 80% to about 90% by weight of the sludge.

The dried sludge is introduced into a reaction chamber, for example gasifier 14, in which it is reacted with oxygen, air or oxygen-enriched air supplied through line 18 at substoichiometric conditions. Suitable reaction chambers for use in the method of this invention include, but are not limited to, cyclonic reactors, rotary kilns, fluidized bed reactors, fixed bed reactors or hybrids thereof. However, any type of contactor apparatus which will accomplish the stated function may be employed. In gasifier 14, the carbonaceous component of the sludge reacts with water present in the sludge and oxygen at elevated temperatures to produce a gaseous composition comprising carbon monoxide and hydrogen as primary components and lesser amounts of carbon dioxide, water vapor and nitrogen. Preferably, this reaction is carried out at temperatures that exceed the melting temperature of the non-carbonaceous components of the sludge. The temperature in gasifier 14 is preferably in the range of about 1700° F. to about 2800° F. A fluxing agent or other additives ranging from about 1% by weight to about 20% by weight of the total amount of non-carbonaceous materials present in the sludge may be employed without adverse impact to reduce the melting temperature of the non-carbonaceous fraction of the sludge. However, this reaction can be carried out in a non-melting mode, which is considered to be within the scope of this invention. In addition, auxiliary fuel may be necessary and can be added to achieve and sustain the target temperatures in the gasifier. The temperature of the gas from gasifier 14 is preferably above about 2000° F. and, thus, may be used in a heat exchanger 15 for the purpose of drying the wet sludge. The temperature of the gases passing through heat exchanger 15 is reduced to about 300° F. to about 500° F.

The melting of the non-carbonaceous material in the sludge is essential to render the residue environmentally benign. After these steps, the cooled residue can be easily disposed of in landfills or it can be used by the construction industry.

As shown in FIG. 1, the methane and carbon dioxide from bio-digesters 10 are mixed with the gas mixture comprising carbon monoxide and hydrogen from gasifier 14 to form a single source of fuel from the renewable resource, i.e. sludge, and burned in either a boiler to produce steam, which, in turn, may be employed in a steam turbine to generate electricity and/or a gas turbine to generate electricity. A micro-turbine 16, or any similar device may also be utilized for this purpose. The energy content of the exhaust gases emanating from any of these conversion devices is recovered by means of heat exchanger 17 and utilized in the dryer 13 to reduce the moisture content of the sludge prior to gasification. Generally, in these conversions, the efficiency of converting heat to electricity is in the range of about 30% to about 50%. This leaves about 50% to about 70% of the heat energy for other purposes. This heat, as previously stated, is employed for drying the residual sludge from the bio-digesters. The quantity of heat present in this stream is more than sufficient to completely dry all of the sludge emanating from the bio-digesters. If electric power is produced from sewage sludge in accordance with the method of this invention, the impact of its water content on process efficiency is minimized and, thus, the highest efficiency is attained. In addition, the solid residue is also converted into material that can safely find use in the construction industry.

In the examples that follow, it is assumed that raw wastewater flowing into a wastewater treatment plant has undergone the following typical treatment steps: screening, primary sedimentation, secondary sedimentation, trickle filter treatment and activated sludge treatment. The sludges collected from the various stages has been thickened toy total solids content of 8% by weight.

SPECIFIC EXAMPLES

Sludge containing about 8% by weight solids is subjected to anaerobic digestion in which 80% of the volatile biodegradable organic solids are converted to a gas mixture containing 65 mol % methane and 35 mol % carbon dioxide. All of these examples are based on the introduction of the equivalent of one ton per hour of dry solids into the digester. Water is removed from the sludge using a filter press resulting in the sludge leaving the filter press having a solids content of about 25% by weight. This sludge is then dried in a dryer. The moisture content of the sludge leaving the dryer can be in the range of 0% to about 50%. The energy required for the dryer can be provided by the cooling of gasifier exit gas, waste heat available from the micro-turbine system, from the combustion of bio-digester gas, or any combination thereof. In this example, as shown in FIG. 1, the sludge is dried using the heat available from the gasifier exit gas and waste heat available from the micro-turbine system.

The dried sludge is then reacted in a slagging gasifier under substoichiometric conditions using air or oxygen or oxygen-enriched air, producing a gaseous composition containing primarily $CO$, $CO_2$, $H_2$, $H_2O$ and $N_2$. The gasifier exit gas is then mixed with the bio-digester gas and fed to micro-turbine 16 where power is generated. The performance of the slagging gasifier depends on its operating conditions and moisture content of the, sludge feed. If no non-carbonaceous materials are present in the sludge, the gasifier may be operated in a non-slagging mode. Several cases are summarized in Table 1 hereinbelow. All of these cases assume the same digester performance as stated above.

Example 1

Sludge is dried in a dryer to a moisture content of 20% and then reacted with oxygen in the reaction chamber (slagging gasifier) at a temperature of about 2400° F. The noncombustible portion of the sludge is melted and then rapidly quenched to render the residue benign to the environment. About 43.42 moles of gas mixture per ton of solids in the raw sludge with a higher heating value (HHV) of about 130 Btu/SCF is produced in the gasifier. The composition of the gas mixture is given in Table 1. This gas is reduced in temperature to about 400° F. and the recovered heat is used for drying the sludge feed to the gasifier. The cooled gas is then mixed with the bio-digester gas and fed to the micro-turbine by which electric power in the range of about 1345 kWh per ton of solids in the raw sludge is generated.

Example 2

As in Example 1, sludge is dried in a dryer to a moisture content of 20% and then reacted with oxygen in the reaction chamber (slagging gasifier), but at a temperature of only about 1800° F. The noncombustible portion of the sludge is melted and then rapidly quenched to render the residue benign to the environment. About 43.42 moles of gas mixture per ton of solids in the raw sludge with an HHV of about 157 Btu/SCF is produced in the gasifier. The composition of the gas mixture is shown in Table 1. This gas is cooled to about 400° F. and the recovered heat is used for drying sludge feed to the gasifier. The cooled gas is then mixed with the bio-digester gas and fed to the micro-turbine where 1385 kWh of electric power per ton of solids in the raw sludge is generated.

Example 3

In this example, sludge is completely dried in a dryer, that is to a moisture content of 0%, and then reacted with oxygen in the reaction chamber (slagging gasifier) at a temperature of about 2400° F. In this case, some steam must be fed to the reaction chamber to provide reaction media. Steam is raised in the system using the available waste heat. The noncombustible portion of the sludge is melted and then rapidly quenched to render the residue benign to the environment. About 43.58 moles of gas mixture per ton of solids in the raw sludge with an HHV of about 147 Btu/SCF is produced in the gasifier. The composition of this gas mixture is also shown in Table 1. This gas is cooled to about 400° F. while the recovered heat is used for drying the sludge feed to the gasifier. The cooled gas is then mixed with the bio-digester gas and fed to the micro-turbine where 1371 kWh of electric power per ton of solids in the raw sludge is generated.

Example 4

As in Example 3, sludge is again completely dried in the dryer to a moisture content of about 0% and then reacted with oxygen in the reaction chamber (slagging gasifier), but at a temperature of only about 1800° F. Some steam is also fed to the reaction chamber to provide reaction media. Steam is raised in the system using the available waste heat. The noncombustible portion of the sludge is melted and then rapidly quenched to render the residue benign to the environment. About 43.58 moles of gas mixture per ton of solids in the raw sludge with an HHV of about 174 Btu/SCF is produced in the gasifier. The composition of the gas mixture is shown in Table 1. This gas is cooled to about 400° F. and the recovered heat is used for drying sludge feed to the gasifier. The cooled gas is then mixed with the bio-digester gas and fed to the micro-turbine by which 1411 kWh of electric power per ton of solids in the raw sludge is generated.

Example 5

In this example, sludge is completely dried in the dryer, that is to a moisture content of 0%, and then reacted with air, as opposed to oxygen, in the reaction chamber (slagging gasifier) at a temperature of 1800° F. Some steam is also fed to the reaction chamber to provide a reacting media. Steam is raised in the system using the available waste heat. The noncombustible portion of the sludge is melted and then rapidly quenched to render the residue benign to the environment. About 79.33 moles of gas mixture per ton of solids in the raw sludge with an HHV of about 81 Btu/SCF is produced in the gasifier. The composition of this gas mixture is also shown in Table 1. This gas is cooled to 400° F. while the recovered heat is used for drying sludge feed to the gasifier. The cooled gas is then mixed with the bio-digester gas and fed to the micro-turbine by which 1370 kWh of electric power per ton of solids in the raw sludge is generated.

TABLE 1

Power Generation Under Various Scenarios*

| Example No. | 1 | 2 | 3 | 4 | 5 |
|---|---|---|---|---|---|
| Oxidant | Oxygen | Oxygen | Oxygen | Oxygen | Air |
| Gasifier Temperature, ° F. | 2400 | 1800 | 2400 | 1800 | 1800 |
| Oxidant Feed, lb | 400 | 342 | 362 | 304 | 1558 |
| Gasifier Gas Made, lb-mole | 43.42 | 43.42 | 43.58 | 43.58 | 79.33 |
| Gas Composition, mole % | | | | | |
| CO | 22.8 | 22.6 | 25.1 | 24.6 | 13.3 |
| $CO_2$ | 16.9 | 17.2 | 14.5 | 15.0 | 8.4 |
| $H_2$ | 16.1 | 24.8 | 19.2 | 28.0 | 10.9 |
| $H_2O$ | 41.2 | 32.5 | 38.2 | 29.4 | 11.9 |
| $N_2$ | 2.3 | 2.3 | 2.3 | 2.3 | 55.0 |
| Gas Heating Value, Btu/SCF | 130 | 157 | 147 | 174 | 81 |
| Bio-Digester Gas Made, lb-moles | 52.90 | 52.90 | 52.90 | 52.90 | 52.90 |
| Gas Composition, mole % | | | | | |
| $CH_4$ | 65 | 65 | 65 | 65 | 65 |
| $CO_2$ | 35 | 35 | 35 | 35 | 35 |
| Power Generated in Micro-turbine, kWh | 1345 | 1385 | 1371 | 1411 | 1370 |

*All flows are based on one ton of solids in raw sludge

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A method for generating electricity comprising the steps of:
   anaerobically digesting sludge, forming a gas mixture of methane and carbon dioxide and a digested sludge;
   removing water from said digested sludge, forming dewatered sludge;
   gasifying said dewatered sludge in a slagging gasifier, forming a gaseous composition comprising carbon monoxide and hydrogen and a residue of non-carbonaceous material; and
   burning said methane, hydrogen and carbon monoxide in an apparatus suitable for generating electricity, resulting in a generation of electricity.

2. A method in accordance with claim 1, wherein said water is removed from said digested sludge by a method selected from the group consisting of filtration, centrifugation, drying and combinations thereof.

3. A method in accordance with claim 1, wherein said methane, hydrogen and carbon monoxide are burned in a micro-turbine.

4. A method in accordance with claim 1, wherein waste heat from said apparatus for generating electricity is used for drying said digested sludge.

5. A method in accordance with claim 1, wherein said solids content of said digested sludge is increased to at least about 50% by weight.

6. A method in accordance with claim 1, wherein said dewatered sludge is gasified by reaction with an oxidant selected from the group consisting of oxygen, air and oxygen-enriched air under substoichiometric conditions at elevated temperatures.

7. A method in accordance with claim 6, wherein said elevated temperature exceeds a melting temperature of a non-carbonaceous component of said dewatered sludge.

8. A method in accordance with claim 6, wherein said elevated temperature is in a range of about 1700° F. to about 2800° F.

9. A method in accordance with claim 6, wherein at least one additive ranging from about 1% by weight to about 20% by weight of a total amount of non-carbonaceous materials present in the sludge is employed for reducing the melting temperature of the non-carbonaceous fraction of the sludge.

10. A method in accordance with claim 1, wherein said gaseous composition is at a temperature in a range of about 1700° F. to about 2800° F. and is used for drying said digested sludge.

11. A method in accordance with claim 6, wherein a pressure in said gasifier is in a range of about 0 psig to about 1500 psig.

12. A method for generating electricity comprising the steps of:
   anaerobically digesting sludge, forming a gas mixture of methane and carbon dioxide and a digested sludge;
   increasing a solids content of said digested sludge to a range of about 50% to about 100% by weight of said digested sludge, forming high solids content sludge;
   gasifying said high solids content sludge, forming a gaseous, composition comprising carbon monoxide and hydrogen and a residue of non-carbonaceous material; and
   burning said methane, hydrogen and carbon monoxide in an energy conversion aparatus suitable for generating electricity, resulting in a generation of electricity.

13. A method in accordance with claim 12, wherein said high solids content sludge is gasified by reaction with an oxidant selected from the group consisting of oxygen, air and oxygen-enriched air under substoichiometric conditions at a temperature in a range of about 1700° F. to about 2800° F.

14. A method in accordance with claim 13, wherein a sensible heat content of said gaseous composition is utilized for increasing the solids content of said sludge.

15. A method in accordance with claim 1, wherein said residue of non-carbonaceous material is melted, producing a molten non-carbonaceous material.

16. A method in accordance with claim 15, wherein said residue of non-carbonaceous material is melted in said slagging gasifier.

17. A method in accordance with claim 12, wherein said residue of non-carbonaceous material is melted in said slagging gasifier, forming a molten non-carbonaceous material.

* * * * *